United States Patent [19]

Radda et al.

[11] Patent Number: 4,528,509
[45] Date of Patent: Jul. 9, 1985

[54] SPATIALLY SELECTIVE NMR

[75] Inventors: George K. Radda, Oxford; John C. Waterton, Runcorn; David G. Gadian, Holcot, all of England

[73] Assignee: National Research Development Corporation, London, England

[21] Appl. No.: 416,066

[22] Filed: Sep. 8, 1982

[30] Foreign Application Priority Data

Sep. 9, 1981 [GB] United Kingdom ............... 8127204

[51] Int. Cl.$^3$ .......................................... G01R 33/08
[52] U.S. Cl. .................................. 324/309; 324/318
[58] Field of Search ............. 324/300, 307, 311, 309, 324/318-320, 322

[56] References Cited

U.S. PATENT DOCUMENTS 3,932,805  1/1976  Abe ........................... 324/309
4,290,019  9/1981  Hutchison ................... 324/309

Primary Examiner—Michael J. Tokar
Attorney, Agent, or Firm—Cushman, Darby & Cushman

[57] ABSTRACT

In a method of high resolution pulsed NMR spectroscopy, the r.f. field is deliberately made inhomogeneous and a special pulse sequence is used to ensure that the received signals emanate predominantly from a selected region of the sample. Thus, the acquisition pulse (70) from which the FID signal (72) results is preceded by a preparatory treatment involving at least one r.f. pulse (66) which is a 180° pulse in respect of nuclei of interest in the selected region, preferably followed by a d.c. pulse (68) giving rise to a magnetic field gradient superimposed on the main alignment field.

6 Claims, 4 Drawing Figures

SPATIALLY SELECTIVE NMR

This invention relates to the spatially selective investigation of the interior of a sample by means of nuclear magnetic resonance (NMR) techniques.

The field of the invention must be understood to be distinguished from the process of NMR imaging, particularly of biological systems, and for this purpose the imaging process will be briefly described. In the human body, water represents 70–80% of the mass of soft tissue and a little over 10% of bone so that the two are readily distinguishable in a NMR experiment in terms of the proton signal strength. In order to localise the source of NMR signals in the sample it is usual to superimpose on the conventional uniform static magnetic field other magnetic fields which vary rapidly with distance and are combined to isolate a small region in which the basic field persists. An image of an area or a volume may then be developed by manipulation of the field gradients to cause the region of interest to be scanned through the sample. This method provides a basis for non-invasive imaging of a human or animal body in vivo in terms of proton density. Further clinical information is available by mapping the proton spin-lattice relaxation time which is sensitive to the particular chemical environment of the water molecules.

Both spatial and spectral resolution are of importance, however, in the investigation of many biochemical and physiological problems in the organs which relate to phosphorus-containing metabolites. In general the proton imaging methods noted in the preceding paragraph cannot provide the spectral resolution between signals from phosphorus atoms of different nuclear shielding which is necessary to distinguish these metabolites. In addition, these methods cannot normally be used to obtain useful data from phosphorus since the signal induced in a $^{31}P$ NMR imaging experiment would be inadequate. High resolution techniques are thus essential for the study of such problems. An experiment has been reported in which in a high resolution pulsed NMR system excitation is effected using a radio-frequency coil applied to the surface of a sample so as to produce deliberately a non-uniform field of limited extent within the sample. The length of the excitation pulse is chosen so as to produce 90° rotation for nuclear spins which are located at points where the component of the r.f. magnetic field perpendicular to the static magnetic field has a particular value; the totality of these points thus constitutes a selected region such that the greater part of the amplitude of the subsequent decay signal must be attributed to nuclei in the selected region. Very useful results have been obtained by this technique but inevitably the signal contains contributions from regions adjacent the selected region in which some significant rotation, less than or greater than 90°, has been produced.

It is an object of the invention to provide improved spatial selectivity in a method of high resolution pulsed NMR spectroscopy using such a r.f. field gradient system.

In accordance with the invention there is provided a method of high resolution pulsed NMR spectroscopy, in which at least part of a sample to be investigated is immersed in a uniform static magnetic field and a signal relating to a given nuclear species is acquired from the sample following irradiation of at least said part of the sample with a pulse of radio frequency energy such that the r.f. magnetic field is inhomogeneous in said part of the sample, characterised in that prior to said irradiation said part of the sample is subjected to a preparatory treatment which involves irradiating it in a similar manner with at least one pulse which is effective to cause 180N° rotation of the magnetisation for those nuclei of said species which are located within a selected region of said part of the sample, N being an integer.

The initial irradiation with one or more 180N° pulses has the effect that nuclei of the given species in the selected region are maintained in a coherent phase relationship at each such pulse while those remote from that region become progressively less coherent. The net transverse nuclear magnetisation for locations other than the selected region is thus much reduced so that the output signal in response to the data acquisition pulse is predominantly due to nuclei in that region.

The selected region will normally approximate to a surface, whose form will depend on the geometry of the r.f. field. This form may for example be made substantially hemispherical or substantially planar by appropriate design of the coil by means of which the r.f. irradiation is effected.

Preferably the preparatory treatment also involves subjecting said part of the sample to an additional magnetic field during a limited period following the or each 180N° pulse (or sequence of such pulses), the additional field having a component parallel to said uniform field which is inhomogeneous in a sense differing from the inhomogeneity of the r.f. field; this may be effected by passing a pulse of direct current through an appropriately shaped and located coil system. The effect of the pulsed d.c. field is to accelerate the decoherence of phase for responsive nuclei outside the selected region, so as to reduce any net contribution they make to the output signal for a given timing of the acquisition pulse following the preparatory treatment. The effect of repetition of the sequence (180N° pulse - d.c. pulse) is to improve the spatial resolution.

As with conventional methods, it will normally be desirable in a given investigation to accumulate data from a series of signal acquisitions carried out in a similar manner on the same sample. For reasons which will be explained more fully below, it will often be advantageous when using methods according to the invention to arrange for one half of the series to be carried out using a preparatory treatment which results in the net magnetisation for those nuclei of said species which are located within said selected region being oriented in one sense parallel to the direction of said uniform field, and the other half of the series to be carried out using a preparatory treatment which results in the net magnetisation for those nuclei of said species which are located within said selected region being oriented in the opposite sense parallel to the direction of said uniform field; it will usually be convenient to arrange for these two types of preparatory treatment to alternate throughout the series, but this is not essential. It will of course be appreciated that the wanted NMR signals arising from the selected region will be of opposite signs for the two halves of the series, so that the data accumulation must involve addition for one half and subtraction for the other; this has the effect of canceling in the overall result possible undesirable contributions which may arise from certain regions of the sample other than the selected region.

Where d.c. pulses are used in the prepartory treatment, it may also in some cases be advantageous to arrange for the duration and/or intensity of these pulses to vary in a random manner from one operation to another of the series, so as to avoid the possibility of coincidental reinforcement of some unwanted contribution to the output signals.

In some cases it may be desired to employ known techniques which involve changing the r.f. phase for the acquisition pulse from one operation of the series to another. In such cases it will usually be convenient (but not essential) to make a corresponding change in the r.f. phase in respect of the 180N° pulses used in the preparatory treatment.

The manner in which the invention may be carried out will be further explained and an embodiment of suitable apparatus will be described with reference to the accompanying drawings in which.

Figure 1:
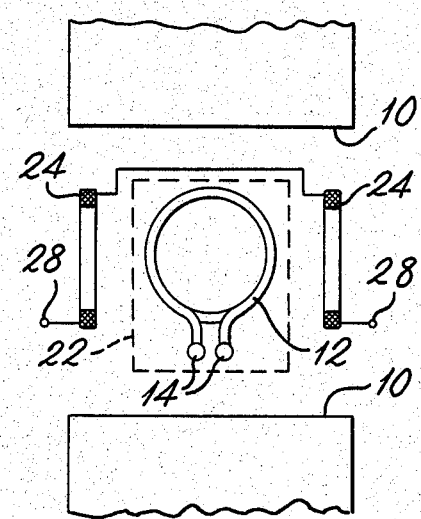
FIG. 1 represents schematically part of an apparatus for carrying out the invention.

Fig. 1 illustrates part of a NMR spectrometer which also includes a conventional transmitter and receiver (not shown). The spectrometer includes a large magnet indicated only by opposing pole pieces 10 between which a strong and highly uniform field $B_o$ is produced. The field extends parallel to the vertical axis of the paper, which will be denoted the Z axis in accordance with the usual convention. A circular r.f. coil 12 is mounted between the pole pieces 10 with its axis perpendicular to the plane of the paper. Coil 12 serves both to apply an excitation signal and to extract an induction decay signal and has terminals 14 for external connection to the transmitter and receiver. A sample holder 22 is arranged for the mounting of an inhomogeneous sample so that the region of interest lies close to the coil 12 on its axis and also within the field $B_o$. The major dimensions of homogeneity of the sample extend parallel to the plane of the paper and the direction of inhomogeneity is along the axis of the coil 12. To enable the sample to be subjected to a pulsed magnetic field gradient there is provided a pair of coaxial circular coils 24 mounted on either side of the holder 22 with their axes corresponding to the horizontal axis of the paper, the coils 24 being wound in opposition and being energised as required from a pulsed d.c. power supply (not shown) via connections 28. The magnetic field produced when the coils 24 are energised has a component parallel to the field $B_o$ which exhibits a gradient in the direction of the axes of these coils.

The transmitter is operative to generate r.f. pulses with the radio frequency set close to the resonance frequencies of the nuclei of interest, i.e. having a value (expressed as an angular frequency) approximately equal to $\gamma B_o$, where $\gamma$ is the relevant gyromagnetic ratio. The pulses are of fixed amplitude but controllable timing and duration, and provision is made for the r.f. phase for a given pulse to be selected from one of four possible values (relative phases 0°, 90°, 180° and 270°); thus by appropriate operation of a programming device a sequence of pulses suitable for a given experiment can be applied to the coil 12 from the transmitter. The resultant signals picked up by the coil 12 are fed to the receiver, in which they are coherently detected; the detected signals are sampled to provide data from which the desired spectrum can be derived by conventional Fourier transformation. Provision is of course made for the accumulation of data from a series of signal acquisitions carried out in a similar manner on the same sample. Preferably the coherent detection system in the receiver includes a pair of phase-sensitive detectors operating in phase quadrature, i.e. with respective reference signals which differ in phase by 90°; in this case it is of course necessary to provide two separate memory devices in the data accumulation system.

Figure 2:
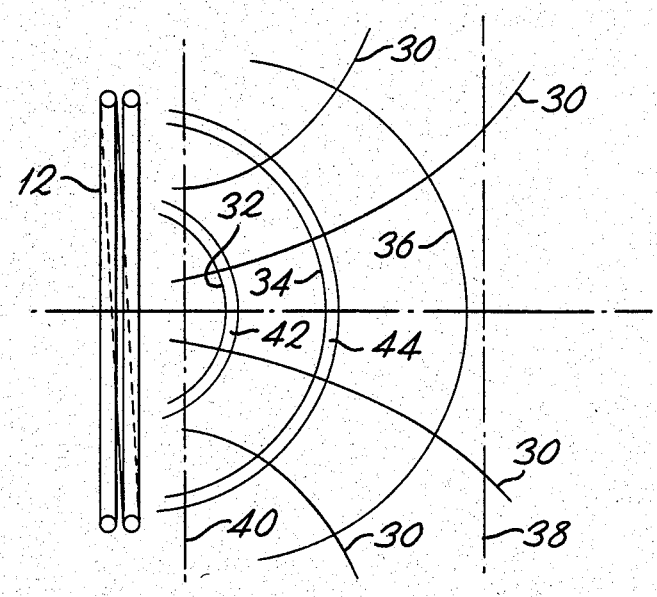
FIG. 2 represents diagrammatically the field pattern of the r.f. coil shown in FIG. 1.

The operation of the apparatus is considered first with reference to FIG. 2 which shows the general form (in that plane perpendicular to the Z axis which contains the axis of the coil 12) of the r.f. magnetic field which is generated when the coil 12 receives an excitation pulse. The coil 12 serves to provide a field which causes nutation of the spins of magnetic nuclei in the sample, as does the r.f. coil of a conventional NMR spectrometer used for making measurements on a homogeneous sample. In the latter context, however, the coil would normally be designed so that the sample is exposed to a uniform r.f. field. In the present case it is required deliberately to produce a field gradient through the sample. In FIG. 2, the flux pattern is indicated by lines 30, and the field profiles (i.e. lines of constant intensity) are indicated by the lines 32, 34 and 36. Although the field is rotationally symmetric with respect to the axis of the coil 12, it should be noted that the parameter of interest is the value of that component ($B_1$) of the field which is directed perpendicular to the Z axis, and this does not exhibit the same rotational symmetry since for all points outside the plane of FIG. 2 there is a non-zero component of the field directed parallel to the Z axis. Thus the surfaces of constant $B_1$ (whose traces in the plane of FIG. 2 correspond to lines such as 32 to 36) are of somewhat distorted spherical shape. The location of the sample is indicated by the lines 38 and 40 in FIG. 2, and it will be appreciated that this is chosen so that the region of interest coincides approximately with a particular surface of constant $B_1$; in the subsequent description it will be assumed that this is the surface corresponding to the line 34. In practical terms, it is appropriate to consider the operation in relation to layers of finite thickness corresponding to the surfaces of constant $B_1$; two such layers are indicated at 42 and 44 in FIG. 2.

Before considering the experimental procedure, the theoretical basis from which the procedure is developed will be reviewed briefly. The field $B_o$ may be termed an alignment field because in the equilibrium state the nuclear spins precess about the direction of the field at the Larmor frequency and produce a net magnetisation in that direction. Precession occurs in random phase so that the componets of transverse magnetisation (perpendicular to the Z axis) sum to zero. As is conventional, the effect of applying a r.f. pulse having a component $B_1$ of magnetic field perpendicular to $B_o$ can most conveniently be considered in terms of a reference frame rotating about the Z axis at the radio frequency, so that $B_1$ can be represented by a vector oriented in a given direction in the XY plane, this direction being dependent on the r.f. phase and conveniently being taken as the X axis for zero relative phase. In this rotating frame the nuclear magnetisation precesses about the direction of $B_1$ with an angular frequency equal to $\gamma B_1$. The spins are ordered in phase under the influence of the r.f. field so that as precession proceeds through an angle $\theta$ during the pulse a net component of transverse magnetisation is developed which varies with the sine of $\theta$; the transverse component thus has a maximum value when $\theta$ is 90° and is zero when $\theta$ is 180°. A particular pulse is (as usual) denoted by the relevant value of $\theta$ (equal to $\gamma B_1 t_p$ radians, where $t_p$ is the duration of the pulse); for example a 90° pulse is one for which $t_p = \pi/2\gamma B_1$.

The free induction decay signal which arises following excitation with a r.f. pulse will of course be of maximum strength for a 90° pulse, but in practice it will often be appropriate to use a smaller value of $\theta$ (possibly as low as 30°). It is also relevant to note that the range of frequencies over which effective excitation occurs for a pulse of duration $t_p$ has a width of the order of $1/t_p$, and $t_p$ must of course be made sufficiently small to ensure that this covers the full range of chemically shifted resonance frequencies in respect of the nucleus of interest for which spectral data are required.

In the present case, the foregoing general considerations are of course applied in the context of a situation in which the value of $B_1$ is deliberately caused to vary through the sample. Referring again to FIG. 2, the question of spatial discrimination will now be considered in relation to the layer 44 (which consitutes the selected region from which one wishes to obtain signals) and the layer 42 (which represents a region from which unwanted signals may arise); the values of $B_1$ for the layers 44 and 42 will be respectively denoted $B_1(S)$ and $B_1(U)$, and a like convention will be used in respect of the angle $\theta$. Suppose that with the sample initially in an equilibrium state a r.f. pulse is applied such that $\theta(S)$ is 90°, so as to maximise the decay signal from layer 44. Then $\theta(U)$ will be greater than 90°, $B_1(U)$ being greater than $B_1(S)$ since layer 42 is closer than layer 44 to the centre of coil 12. In general however, a partial response will still be obtained from layer 42, since the spins in layer 42 remain coherent during excitation and the decay signal contributed by layer 42 is only reduced because $\theta$ has exceeded 90°. It has been appreciated by the inventors, however, that coherence may be preserved in layer 44 while incoherence is allowed to develop in layer 42 by a preparation stage involving the application of at least one pulse for which $\theta(S)$ is 180°. Such a pulse may suitably be denoted as a 180°(S) pulse.

Figure 3:
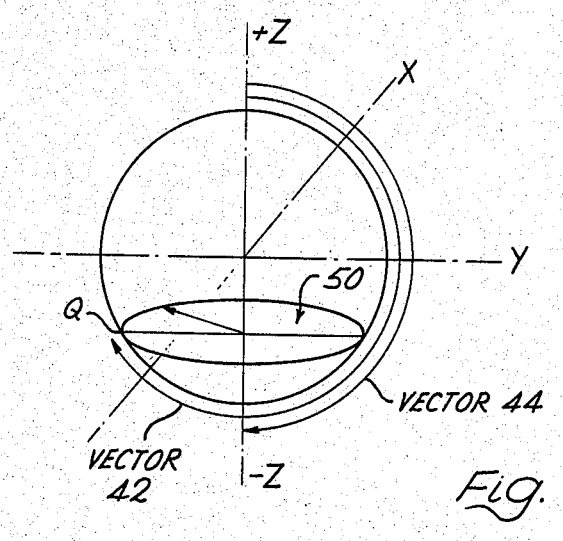
FIG. 3 represents diagrammatically the rotation of nuclear magnetisation in the field of FIG. 2.

Referring now to FIG. 3 the sequence of operation will be indicated first for an experiment involving a value of the effective transverse relaxation time $T_2^*$ which is small relative to the spin-lattice relaxation time $T_1$. It will be appreciated that such a condition inherently limits the achievable spectral resolution and may be regarded as an extreme example of the range of application of the present invention. Initial alignment of spins in the $+Z$ direction is assumed in layers 42 and 44. On applying a 180°(S) pulse on the X axis in the rotating frame the magnetisation vector in layer 44 is rotated in the YZ plane from $+Z$ to $-Z$ and a subsequent acquisition pulse (with $\theta(S)$ in the range 30–90°) produces a transverse component of magnetisation in the $-Y$ direction and a consequent free induction decay signal. In layer 42 the first pulse causes a rotation of the magnetisation vector past the $-Z$ direction to an angle represented by the position Q. Relaxation then occurs in the plane 50 which contains the point Q and lies parallel to the XY plane. Since $T_2^*$ is small, phase decoherence occurs rapidly and on applying the acquisition pulse any transverse magnetisation component which is generated is relatively small. In the case where $\theta(S)$ is 90° for the acquisition pulse, it is further reduced because $\theta(U)$ for this pulse is greater than 90°. Repetitions of the 180°(S) pulse before acquisition will progressively diminish any contribution to the decay signal which is made by the nuclei of layer 42, and typically it would be appropriate to use a total of four or five 180°(S) pulses.

More commonly the materials of interest for high-resolution spectroscopy will have higher natural values of transverse relaxation time $T_2$ and great care will be taken in the experimental arrangement to ensure that the effective value $T_2^*$ is as large as possible. Very little loss of phase coherence will then occur during relaxation in plane 50 of the magnetisation representing layer 42 and repeated 180°(S) pulses will fail to produce significant saturation. In this situation it is proposed to apply a magnetic field gradient, by means of a d.c. pulse on coils 24 (FIG. 1), following each 180°(S) pulse. It will be appreciated from the description referring to FIG. 1 that the coils 24 are so arranged that when they are energised, nuclei at different parts of layer 42 are exposed to different values of field parallel to the Z axis.

To consider the effect of the d.c. pulsed field it will be assumed as previously described with reference to FIG. 3 that a 180°(S) pulse has rotated the magnetisation of nuclei in layer 44 to the $-Z$ position and that for layer 42 to position Q. On now applying the field gradient the spins in equilibrium at $-Z$ are unaffected. The spins in layer 42 are initially precessing in plane 50 at substantially the same rate so that they remain in phase. Such spins are now exposed to a magnetic field which varies with position in the layer 42 and a rapid loss of phase coherence occurs which may be sufficient to reduce the contribution to the output, following an acquisition pulse, to a tolerably low level. Alternatively the sequence of a 180°(S) pulse and a d.c. gradient pulse may be repeated one or more times before acquisition.

A possible complication may arise in cases where there is in the sample a region where $B_1$ has a value equal to $2B_1(S)$, since for such a region the 180°(S) pulse will have the effect of a 360° pulse so that coherence is preserved. This is of little significance where $\theta(S)$ is chosen to be 90° for the acquisition pulse, since the acquisition pulse will then be a 180° pulse for the region concerned, but may give rise to a substantial unwanted contribution to the decay signal in cases where $\theta(S)$ for the acquisition pulse differs significantly from 90°. If, however, one takes the difference between two signals respectively acquired after preparatory treatments involving n and (n+1) 180°(S) pulses, the contributions to the two signals from the selected region will reinforce each other while the contributions from any region where $B_1$ has a value equal to $2B_1(S)$ (and also from any region where $B_1$ is small) will effectively cancel each other. In theory one should also have regard to the possible existence of regions where the value of $B_1$ is a greater multiple of $B_1(S)$, but in practice it will normally be possible to arrange the geometry of the r.f. field so that such regions do not occur within the part of the sample which is subjected to the field $B_o$.

Where data are accumulated from a series of signal acquisitions, it is of course necessary to allow appropriate intervals for relaxation to the equilibrium state between successive operations of the series. The same r.f. phase will be used throughout the series where a single phase-sensitive detector is used in the receiver, but where the phase quadrature detection system is employed it is preferable to use a known procedure in which the four possible values of r.f. phase are used for equal numbers of the signal acquisitions, with the data being appropriately allocated between the two memory devices. As explained in British Patent Specification No. 1496886, this procedure enables errors arising from inequalities in gain and phase shift error between the two channels of the receiver to be compensated and also enables systematic noise to be cancelled. When using the four-phase procedure in conjunction with the differencing procedure referred to in the last preceding paragraph, a total of eight different types of operation will be involved, which may conveniently be arranged to occur in a cyclic sequence. The relevant characteristics for the eight types of operation are indicated in the Table below; denoting the two detectors as $D_1$ and $D_2$ and the two memory devices as $M_1$ and $M_2$, column (a) indicates the relative r.f. phase (assumed to be the same for the 180°(S) pulses in the preparatory treatment as for the acquisition pulse), column (b) indicates whether the number of 180°(S) pulses in the preparatory treatment is odd or even, and columns (c) and (d) indicate to which of the memory devices the data derived respectively via the detectors $D_1$ and $D_2$ are applied, together with the appropriate signs for application of the data.

TABLE

|    | (a)  | (b)  | (c)      | (d)      |
|----|------|------|----------|----------|
| 1. | 0°   | Even | $M_1(+)$ | $M_2(+)$ |
| 2. | 0°   | Odd  | $M_1(-)$ | $M_2(-)$ |
| 3. | 90°  | Even | $M_2(+)$ | $M_1(-)$ |
| 4. | 90°  | Odd  | $M_2(-)$ | $M_1(+)$ |
| 5. | 180° | Even | $M_1(-)$ | $M_2(-)$ |
| 6. | 180° | Odd  | $M_1(+)$ | $M_2(+)$ |
| 7. | 270° | Even | $M_2(-)$ | $M_1(+)$ |
| 8. | 270° | Odd  | $M_2(+)$ | $M_1(-)$ |

Figure 4:
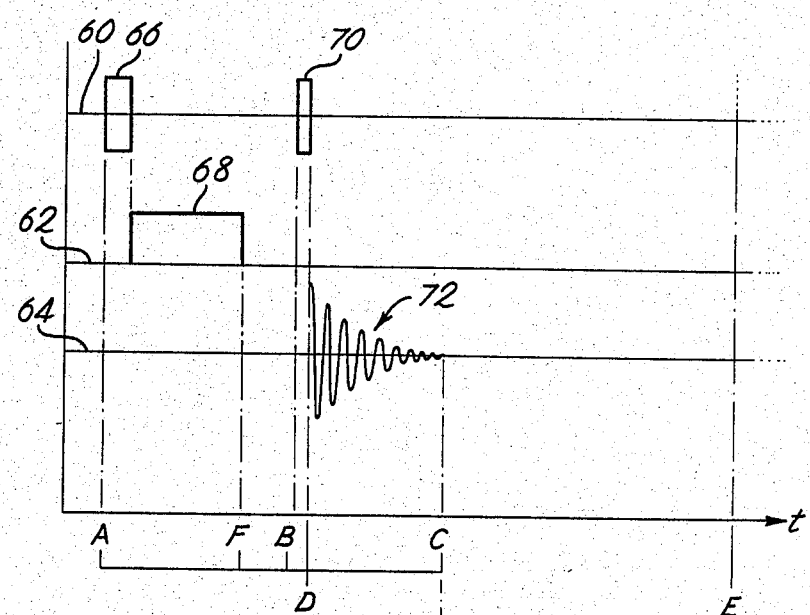
FIG. 4 represents an experimental time sequence in carrying out the invention.

The general conditions and overall time scale of a suitable form of a $^{31}P$ experiment will be indicated with reference to FIG. 4. For an aligment field $B_o$ of about 40kG the Larmor frequency is close to 70 MHz and the radio frequency is set accordingly. For a particular selected region the duration of a 180°(S) pulse might suitably be determined as 55µs. In FIG. 4 the horizontal axis represents time (but not to scale) and the vertical axis represents amplitude. Horizontal scales 60, 62, 64 respectively represent operation of the transmitter, the d.c. pulse source and the receiver. A complete acquisition sequence occupies a period AE comprising a preparation stage AB, an acquisition stage BC and a relaxation stage DE which overlaps the whole decay period of stage BC. Stage AB starts with a 180°(S) pulse 66 which is immediately followed by a d.c. pulse 68 a few ms in length. The operation of the instrument may make necessary the provision of a short delay FB. In order to improve the spatial resolution of the selected region, stage AB should be repeated several times but this repetition should not be carried to the point of making the size of the selected region so small as to result in an insignificant received signal. In some cases the spin-lattice relaxation time may also impose a limit on the time available for repetition. Suppose stage AB is performed n times. An acquisition pulse 70 of length chosen to give the desired value of $\theta(S)$ in the range 30°-90° is then applied and a free induction decay signal 72 is observed in the receiver over a period DC which might typically extend up to 100 ms (say) or three times $T_2^*$. Substantially complete spin-lattice relaxation must occur before the sequence is repeated and stage DE is of a length up to $3T_1$ (say, 1s or more). If now a second acquisition sequence is run which includes (n+1) performances of stage AB and the difference is taken between the outputs from the two sequences the contribution from regions having $B_1$ twice $B_1(S)$ is eliminated. The effect of regions of small $B_1$ is also eliminated. Such a pair of acquisition sequences is taken for each of a series of r.f. phase values differing by 90° in order to compensate for system errors, etc., as mentioned above.

On the basis of the explanation which has been given of the physical mechanism of phase decoherence induced during the preparatory treatment it will be apparent that in accordance with the invention the 180°(S) pulses may be replaced by pulses or sequences of pulses of equivalent effect. For example each 180°(S) pulse may be replaced by a 360°(S) pulse (or one for which $\theta(S)$ is a larger multiple of 180°), or by a pair of successive 180°(S) pulses applied along the X and Y axes respectively (i.e. differing in r.f. phase by 90°). In both cases fewer d.c. pulses would be needed for a given effect than when using simple 180°(S) pulses. The saving in time may be important in observing an event having a short lifetime in a subject with short nuclear spin-lattice relaxation times. If it is desired to use the differencing procedure in these cases, a single 180°(S) pulse (followed by a d.c. pulse) should be added to the preparatory treatment for one of the relevant pair of acquisition sequences but not the other.

A further degree of localisation is made possible by incorporating in the experiment the known technique of field profiling of the alignment field $B_o$ in which a non-uniform static field is superimposed on $B_o$ to produce a steep field gradient except in a limited volume encompassing the selected region.

In the arrangement described above, the value of $\theta(S)$ for a given r.f. pulse is determined by choice of the duration of the pulse. It would of course be possible instead to use pulses of fixed duration and vary the pulse amplitude to effect the required changes of $\theta(S)$, although this might be less convenient in practice.

We claim:

1. A method of high resolution pulsed NMR spectroscopy, in which at least part of a sample to be investigated is immersed in a uniform static magnetic field and a signal relating to a given nuclear species is acquired from the sample following irradiation of at least said part of the sample with a pulse of radio frequency energy such that the r.f. magnetic field is inhomogeneous in said part of the sample, characterized in that prior to said irradiation said part of the sample is subjected to a preparatory treatment which involves irradiating it in a similar manner with at least one pulse which is effective to cause 180N° rotation of the magnetisation for those nuclei of said species which are located within a selected region of said part of the sample, N being an integer.

2. A method according to claim 1, in which said preparatory treatment also involves subjecting said part of the sample at least once, during a limited period following a r.f. pulse, to an additional magnetic field having a component parallel to said uniform field which is inhomogeneous in a sense differing from the inhomogeneity of the r.f. field.

3. A method according to claim 1 or 2, in which a series of signal acquisitions is carried out on said sample in a similar manner but with the preparatory treatment differing between two halves of the series such that for one half the preparatory treatment results in the net magnetisation for said nuclei being oriented in one sense parallel to the direction of said uniform field while for the other half the preparatory treatment results in the net magnetisation for said nuclei being oriented in the opposite sense parallel to the direction of said uniform field, data derived from said series of signal acquisitions being accumulated with opposite signs allocated to the data in respect of said two halves of the series.

4. A method of high resolution pulsed NMR spectroscopy, comprising the steps of:
   immersing at least part of a sample to be investigated into a uniform static magnetic field;
   irradiating at least said part of a sample with a radio frequency pulse to thereby generate an inhomogeneous magnetic field in said part of a sample;
   acquiring a signal related to a given nuclear species from said part of a sample after said irradiating; and
   preparing said part of a sample prior to the irradiating step by subjecting said part to a prepartory pulse effective to cause 180N° rotation of the nuclei magnetization of said given species which are located within a selected region of said part of the sample, where N is an integer.

5. A method according to claim 4, wherein said preparing step further includes the step of at least once further subjecting, within a predetermined time period following said radio frequency pulse, said part of the sample to a further magnetic field having a component which is parallel to said uniform field and which is inhomogeneous in a sense different from the inhomogeneity of said radio frequency pulse field.

6. A method as in claim 5, further comprising the steps of:
   repeating a series of said irradiating, acquiring and preparing steps wherein a succession of said parallel components of said further magnetic field alternate directions to thereby form two halves of said series; and
   deriving data from said series of acquired signals by accumulating said signals, with opposite signs allocated to signals from opposing halves of said series.

* * * * *